United States Patent [19]

Kubota et al.

[11] 4,398,007

[45] Aug. 9, 1983

[54] DENTURE-BASE RESIN COMPOSITION AND METHOD FOR USING THE SAME

[75] Inventors: Takao Kubota, Sayama; Shigenobu Kusakai, Tokyo, both of Japan

[73] Assignee: G-C Dental Industrial Corp., Tokyo, Japan

[21] Appl. No.: 199,625

[22] Filed: Oct. 22, 1980

[51] Int. Cl.³ ............................................ C08F 130/08
[52] U.S. Cl. .................................... 526/273; 433/199; 433/201; 433/202; 433/212; 526/279; 528/26
[58] Field of Search ............... 260/998.11, 42; 106/36; 433/199, 201, 202, 212; 526/273, 279; 528/26

[56] References Cited

U.S. PATENT DOCUMENTS 3,706,697 12/1972 Backderf .............................. 528/26

FOREIGN PATENT DOCUMENTS 47-39198 10/1972 Japan .

OTHER PUBLICATIONS

Journal of the Japan Society for Dental Apparatus and Materials, vol. 19, No. 47, Jul. 1978, pp. 179–185.
The Journal of the Japan Prosthodontic Society, vol. 22, No. 3, Aug. 1978, pp. 19-525-25-531.
The Journal of the Japan Research Society of Dental Materials and Appliances, vol. 34, No. 3, 1977, pp. 200–204.

*Primary Examiner*—J. Ziegler
*Attorney, Agent, or Firm*—Oblon, Fisher, Spivak, McClelland & Maier

[57] ABSTRACT

The denture-base resin composition of the present invention contains a liquid component obtained by incorporation of 0.5 to 20% by weight of a particular silane compound and 0.5 to 10% by weight of a unsaturated carboxylic acid into a methyl methacrylate monomer. Examples of the silane compound used in the present invention includes γ-glycidoxypropyltrimethoxysilane, γ-glycidoxypropyltriethoxysilane, γ-methacryloxy-propyltriethoxysilane, etc. The liquid component may be mixed with a methyl methacrylate polymer in a mixing ratio (by weight) of 1:3 to 3:1.

4 Claims, No Drawings

DENTURE-BASE RESIN COMPOSITION AND METHOD FOR USING THE SAME

BACKGROUND OF THE INVENTION

The present invention is concerned with a denture-base resin composition and a method for using it.

As is well-known, dentures having a metal base is more tough, yet less breakable as compared with those composed exclusively of methyl methacrylate resin. The metalic denture can then be made so thin that the resulting denture produces a more natural "feel" to the patient while in service, is free from any water absorption properties, and is kept highly dimensional stable in use. In addition, the denture of the above-mentioned type has numerical advantages; its base has no or little irritating effect; it is compatible to the mouth tissues to the extent that it will not become unsanitary; it shows good thermal conductivity without sacrificing a kind of sensitivity to temperature or taste; it has sufficient strength to resist all normal masticating stresses; and the like. Thus, the denture of this type has spread with the years.

At the present time, metal materials that are used with any degree of success for denture-base materials include gold alloys, gold/silver/palladium alloys, platinum alloys, cobalt/chromium alloys, nickel/chromium alloys, 18-8 stainless-steel wrought alloys etc. Among these alloys, the cobalt/chromium or nickel/chromium alloys are becoming widespread since they are light in weight, say, about one half of the density of the gold alloys, and are very strong, say, about twice the Young's modulus of elasticity. In addition, they are inexpensive and excel in the resistance to discoloration. Artificial teeth used with these metal bases include porcelaineous and resinous teeth; however, preference is generally given to the porcelaineous teeth in view of hardness, wear resistance, harmlessness etc.

In some cases, the metal base may be formed as an integral piece from a metal. In most of the dentures having a metal base that are now available, an alveolus portion for fixing artificial teeth in place and a portion exposed to the inside of the cheek within the mouth are composed of a resin while a portion on the palate side and a connecting part are formed of a metal. Thus, advantage is taken of both metal and resin.

A methyl methacrylate resin is now widely used as a denture-base resin material. Indeed, however, this methyl methacrylate resin shows no chemical adhesion to dental metals or porcelaineous teeth at all. Although various proposals have been made to establish a mechanical connection between the resin and the metal or porcelaineous teeth, there is still left much to be desired. Typically, when the denture receives external forces such as masticating stresses in the mouth during use, the junction between the metal and the resin so-called finishing line cracks to cause separation of one from the other, thus resulting in discoloration and contamination of the resin, emission of an offensive odor and the like.

The necessity of maintenance of such a mechanical connection inevitably renders the denture design and the casting work complicated and difficult. In some cases, polishing of dentures may cause breakage of a thin portion of the junction between it and the metal. Use of retention beads in the junction imposes a certain limitation upon the color tone of the denture. As there is no choice but to cover the muscous surface of the denture base with a metal, it is impossible to effect lining of resin, often referred to as the so-called relining, even when adaptability of the base with the metal becomes unfit.

When dentures are fabricated from porcelaineous teeth and conventional denture-base resin, reliance is put upon either retainer means comprising gold pins set in the surface of the denture base or mechanical retention means using holes, since the porcelaineous teeth do not show any chemical adhesion to the base resin at all. This often causes breakage of the procelaineous teeth due to the concentration of stresses to part thereof held by said retainer means, this resulting in falling-off of the procelaineous teeth from a given place in the mouth during use, as reported in literature.

In addition, accumulation of the mouth fluids and occurrence of bacteria take place in the crevices in the interface of the resin base and the porcelaineous teeth during use, leading to discoloration of the denture and emission of an offensive odor.

With a view to eliminating the above-mentioned defects, it has been attempted to make a chemical bond between the porcelaineous teeth or metal and the base resin material.

Typically, it has been reported that the surface of a metal is etched with an inorganic acid, coated with adhesives and laminated with a methacryl resin. Alternative process using 4-methacryloxyethyl trimellitic acid have also been reported. However, these processes often offer several problems; they result in considerable drops in efficiency and marked variations in the adhesion to the cobalt/chromium alloys and the nickel/chromium alloys. In these processes, any adhesion to the porcelaineous teeth is not obtained at all.

In order to bond the base resin to the porcelaineous teeth, it has been reported to incorporate a silane compound into the methyl methacrylate. With this process, it is possible to bond the base to the porcelaineous teeth, but it is difficult to bond the base to the metal. There are also considerable variations in the adhesive force.

On the other hand, there is well-known in the art such a composition that shows adhesion only to the cobalt or nickel/chromium alloys or the porcelaineous teeth; however, such a composition that is simultaneously displays strong chemical adhesion to both the cobalt or nickel/chromium alloys and the porcelaineous teeth is not still revealed in public.

SUMMARY OF THE INVENTION

Surprisingly, it has now been found to obtain a denture-base resin composition showing strong chemical adhesion to both the cobalt or nickel/chromium alloys and the porcelaineous teeth by allowing a particular silane compound and a unsaturated carboxylic acid to co-exma methyl methacrylate monomer.

The present invention provides a novel denture-base resin composition having chemical adhesion with respect to porcelaineous teeth and dental cobalt or nickel/chromium alloys without having an adverse influence on the excellent working and physical properties of a denture-base methyl methacrylate material that is widely available in dentistry. The novel composition of the present invention can be put to use without recourse to any mechanical retainer means that are used in the prior art for the purpose of holding the porcelaineous teeth and the metal in place.

DETAILED DESCRIPTION OF THE INVENTION

According to the present invention, the physical and chemical properties, such as resistances to fracturing, impact, and solvents, of the denture-base methacryl material that is widely available in dentistry can substantially be improved without sacrificing numerical advantages thereof, such as good appearance, working properties and adhesion to resin teeth. According to one embodiment of the present invention, it has been found that the composition containing 50 ppm of hydroquinone, can be stored for two or more years without curing.

More specifically, the denture-base composition of the present invention contains a liquid component obtained by incorporation of 0.5 to 20% by weight of a particular silane compound (to be defined later) and 0.5 to 10% by weight of a unsaturated carboxylic acid into a methyl methacrylate monomer. This liquid component is mixed with a methyl methacrylate polymer in a weight ratio of 1:3 to 3:1, and the resultant mixture is shaped into a denture form in a conventional manner known in dentistry. Fabrication of the denture comprising a metal plate and porcelaineous teeth with such a composition will now be explained. When the resin dough is placed under pressure and preheated, the unsaturated carboxylic acid first produces an effective action, say, cleaning or etching effect, on the resin-bonding surface of the metal or porcelaineous teeth to activate the bonding surface, following the orientation of silane molecule on the surface. Subsequent polymerization of the methyl methacrylate monomer causes the remaining components to be simultaneously polymerized, thereby making a firm bondage. The actions of these components are very effective since they are exerted without causing the bonded surface to be exposed to atmosphere.

The particular silane compound referred to herein is expressed by the general formula:

$$(AR_c)_n-\underset{\underset{R'_b}{|}}{Si}-D_{4-n-b}$$

wherein
D: a hydrolyzable groups
n: an integer of 1, 2 or 3
b: an integer of 0, 1 or 2
n+b: an integer of 1, 2 or 3
R': a group selected from the group consisting of monovalent hydrocarbon groups
R: an alkylene group having 1 to 4 carbon atoms
c: an integer of 0 or 1

A: 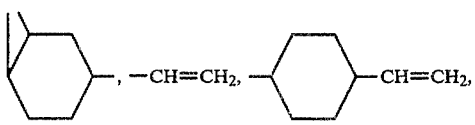

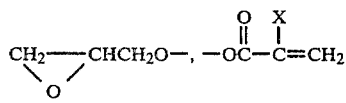

wherein X: a hydrogen atom or a hydrocarbon group having 1 to 6 carbon atoms. In the above-mentioned general formula, D may be any hydrolyzable group. The number of the group D in the silane compound may be 1, 2 or 3, but preference is given to 3. The group D may be, for instance, methoxy, ethoxy, propoxy, isopropoxy or the like group. The group R' may be any monovalent hydrocarbon groups, including methyl, ethyl, propyl, butyl and the like group. The methyl group is recommendable. The letter b may be 1, 2 or 0.

The number of the group ARc may be 1, 2 or 3. In other words, n may be 1, 2 or 3 but should preferably be 1. The group represented by R is a divalent $C_{1-4}$ alkylene group bonded to a silicon atom, such as methylene, ethylene, trimethylene, propylene and the like group. c may be 1 or 0 that means the absence of the group R. A is bonded to the group R except the case where it is directly bonded to a silicon atom, say, c=0. A may be

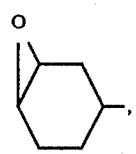

—CH=CH₂,

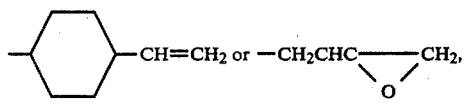

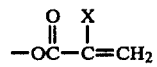

When c=0, A stands for —CH=CH₂ or

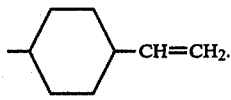

The letter X in the group

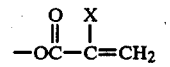

may be a $C_{1-6}$ hydrocarbon group. In this case, an ester group is present in the compound. For instance, X includes methyl, ethyl, isopropyl, butyl and the like group.

Some of the compounds falling under the foregoing definition are commercially available, including γ-glycidoxypropyltrimethoxysilane, γ-glycidoxypropyltriethoxysilane, γ-methacryloxypropyltrimethoxysilane, γ-methacryloxypropyltriethoxysilane, vinyltriethoxysilane, β-(3,4-epoxycyclohexyl)ethyltrimethoxysilane, vinyl-tris(β-methoxyethoxy)-silane. Among these compounds, use is most preferably made of γ-methacryloxypropyltrimethoxysilane.

The unsaturated carboxylic acids used in the present invention may be both a unsaturated monocarboxylic acid and a unsaturated polycarboxylic acid. For instance, use is made of acrylic, methacrylic, chromenic, linolic, undecenoic, β-2-furylacrylic, cinnamic, sorbic, fumaric, maleic and citraconic acids.

Examples of the present invention were carried out under the common conditions set forth below. For comparison, these examples are summed up in terms of adhesion and transverse strength in a Table to be given later.

As a powdery component, use was made of a PMMA polymer (polymethyl methacrylate; particle size: 120–200 Tyler meshes) containing 0.1% B.P.O. (benzoyl peroxide). The PMMA powdery component was mixed with the liquid component specified in the Examples in a mixing ratio (by weight) of 1:2 to form a dough. The dough was pre-polymerized at 70° C. for 30 minutes in the conventional manner, and was polymerized and heated at 100° C. for 30 minutes. As mentioned above, these results are set forth in the Table. From these result, it has been found that the products according to the present invention are considerably superior in the adhesion and physical properties to samples obtained from a commercially available monomer.

In examination of the adhesion of the product with respect to a metal, a 5×5×5 mm mound of wax was formed on the center of a 10×10×2 mm metal test piece that was polished with a chromium oxide abrasive, and was invested in a plaster mold in the conventional manner. After setting of the plaster, the wax was flushed out. The thus formed negative model was washed and filled with a resin sample for polymerization.

In estimation of the adhesion of the product with respect to porcelaineous teeth, reliance was put upon JIS T6511 Test Standard. When the concentration of the silane compound is less than 0.5% by weight, the adhesion strength with respect to the porcelaineous teeth is less than 5 Kg, which means that there is a fear that falling-off of the porcelaineous teeth takes place in use. At a concentration of the silane compound exceeding 20% by weight, the product has a deflexion of more than 6 mm under 5 Kg load in the transverse strength test, and does not meet JIS T 6501 Standard so that it is no longer used for the practical purpose. When the concentration of the unsaturated carboxylic acid is less than 0.5% by weight, the adhesion strength of the product with respect to the cobalt/chromium alloy is less than 40 Kg/cm$^2$. In this case, the unsaturated carboxylic acid produces no effect. At a concentration of more than 10% by weight, the product has a transverse strength of less than 5 Kg, and is not used for the practical purpose. Thus, best results are obtained when the upper and lower limits of the silane compound and the unsaturated carboxylic acid are 0.5–20% by weight and 0.5–10% by weight, respectively.

Concrete examples of the present invention are given below. The adhesion strength and transverse strength measured in each example are summed up in the Table. However, it will be understood that the present invention is not limited to the figures given in the examples.

EXAMPLE 1

Use was made of a liquid composition prepared by adding 50 ppm of hydroquinone to a mixture of:
Methyl methacrylate monomer—90 parts
γ-methacryloxypropyltrimethoxysilane—6 parts
Undecenoic acid—4 parts

EXAMPLE 2

In place of undecenoic acid in Example 1, methacrylic acid was employed.

EXAMPLE 3

Use was made of a liquid composition prepared by adding 100 ppm of butylated hydroxyparatoluene to a mixture of:
Methyl methacrylate monomer—96 parts
γ-methacryloxypropyltrimethoxysilane—3 parts
Acrylic acid—1 part

EXAMPLE 4

Use was made of a liquid composition prepared by adding 50 ppm of hydroquinone to a mixture of:
Methyl methacrylate monomer—90 parts
Ethylene glycol dimethacrylate—1 part
γ-methacryloxypropyltrimethoxysilane—6 parts
Citraconic acid—3 parts

EXAMPLE 5

Use was made of a liquid composition prepared by adding 50 ppm of hydroquinone to a mixture:
Methyl methacrylate—91 parts
γ-methacryloxypropyltrimethoxysilane—5 parts
4-methacryloxyethyl trimellitic acid—3 parts

EXAMPLE 6

In Example 3, γ-glycidoxypropyltrimethoxysilane was used as the silane compound.

EXAMPLE 7

In Example 3, vinyltriethoxysilane was used as the silane compound.

EXAMPLE 8

In Example 3, β-phenylethyltrimethoxysilane was used as the silane compound.

EXAMPLE 9

In Example 3, 2% by weight of dimethylparatoluidine were added to the methyl methacrylate monomer. The resultant liquid composition was allowed to cure at room temperature without heating.

EXAMPLE 10

In Example 3, the acrylic acid was not used.

EXAMPLE 11

In Example 3, the silane compound-γ-methacryloxypropyltrimethoxysilane-was not used.

EXAMPLE 12

Use was made of a commercially available denture-base material.

TABLE

| Examples | Adhesion | | | Transverse Strength JIS T 6501 (Kg) |
|---|---|---|---|---|
| | Ni/Cr Alloys (Kg/cm$^2$) | Co/Cr Alloys (Kg/cm$^2$) | Porcelaineous Teeth (without any retention) (Kg) | |
| (1) | 180 | 167 | 35 | 8.0 |
| (2) | 210 | 220 | 38 | 9.0 |
| (3) | 213 | 210 | 35 | 8.5 |
| (4) | 190 | 187 | 37 | 8.0 |
| (5) | 210 | 214 | 35 | 8.5 |
| (6) | 185 | 174 | 35 | 7.5 |
| (7) | 158 | 135 | 33 | 8.0 |

TABLE-continued

| Examples | Adhesion | | | Transverse Strength JIS T 6501 (Kg) |
|---|---|---|---|---|
| | Ni/Cr Alloys (Kg/cm²) | Co/Cr Alloys (Kg/cm²) | Porcelaineous Teeth (without any retention) (Kg) | |
| (8) | 165 | 121 | 35 | 8.0 |
| (9) | 130 | 105 | 28 | 8.0 |
| (10) | 35 | 40 | 32 | 8.0 |
| (11) | 20 | 15 | 0 | 5.5 |
| (12) | 0 | 0 | 0 | 5.5 |

What is claimed is:

1. A denture-base resin composition comprising a methyl methacrylate monomer containing 0.5 to 20% by weight of a particular silane compound expressed by the general formula:

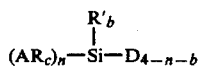

wherein
  D: a hydrolyzable group
  n: an integer of 1, 2 or 3
  b: an integer of 0, 1 or 2
  n+b: an integer of 1, 2 or 3
  R': is a monovalent hydrocarbon group
  R: an alkylene group having 1 to 4 carbon atoms
  c: an integer of 0 to 1

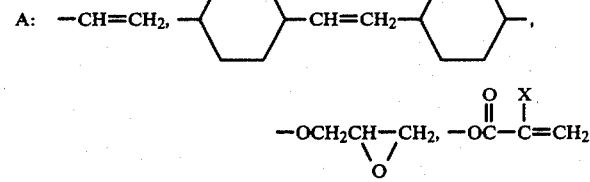

wherein X: a hydrogen atom or a hydrocarbon group having 1 to 6 carbon atoms, and mixed with 0.5 to 10% by weight of a unsaturated carboxylic acid.

2. The denture-base resin composition as recited in claim 1, in which the unsaturated carboxylic acid used is a unsaturated monocarboxylic acid.

3. The denture-base resin composition as recited in claim 1, in which the unsaturated carboxylic acid used is a unsaturated polycarboxylic acid.

4. The denture-based resin composition as recited in claim 2 or 3, in which the methyl methacrylate monomer contains 0.1 to 5% by weight of a cross-linking agent.

* * * * *